(12) United States Patent
Bagley

(10) Patent No.: US 11,896,214 B2
(45) Date of Patent: Feb. 13, 2024

(54) SUTURE BASED CLOSURE DEVICE

(71) Applicant: BOSTON SCIENTIFIC SCIMED, INC., Maple Grove, MN (US)

(72) Inventor: Kevin L. Bagley, Natick, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 321 days.

(21) Appl. No.: 17/217,224

(22) Filed: Mar. 30, 2021

(65) Prior Publication Data
US 2021/0298742 A1 Sep. 30, 2021

Related U.S. Application Data

(60) Provisional application No. 63/002,822, filed on Mar. 31, 2020.

(51) Int. Cl.
A61B 17/04 (2006.01)
A61B 17/06 (2006.01)
A61B 17/062 (2006.01)

(52) U.S. Cl.
CPC ........ *A61B 17/0469* (2013.01); *A61B 17/062* (2013.01); *A61B 17/06061* (2013.01)

(58) Field of Classification Search
CPC .......... A61B 17/0469; A61B 17/06061; A61B 17/062; A61B 17/0625; A61B 2017/0609; A61B 17/0482; A61B 2017/00296; A61B 2017/06047; A61B 2017/0608; A61B 17/06

See application file for complete search history.

(56) References Cited

U.S. PATENT DOCUMENTS

| 5,478,344 | A | 12/1995 | Stone |
| 5,584,861 | A | 12/1996 | Swain et al. |
| 6,086,608 | A | 7/2000 | Ek et al. |
| 6,200,329 | B1 | 3/2001 | Fung et al. |
| 6,494,888 | B1 | 12/2002 | Laufer et al. |

(Continued)

FOREIGN PATENT DOCUMENTS

| CA | 2682488 A1 | 10/2008 |
| DE | 202005022017 U1 | 5/2012 |

(Continued)

OTHER PUBLICATIONS

International Search Report and Written Opinion dated Aug. 20, 2019 for International Application No. PCT/US2019/033748.

(Continued)

*Primary Examiner* — Tan-Uyen T Ho
*Assistant Examiner* — David P Stein
(74) *Attorney, Agent, or Firm* — Seager, Tufte & Wickhem, LLP

(57) ABSTRACT

A suture device includes a suture ring that defines an arcuate channel extending therein. A first arcuate needle passer is slidingly disposed within a first side of the arcuate channel and a second arcuate needle passer is slidingly disposed within a second side of the arcuate channel. An arcuate needle is passable between the first arcuate needle passer and the second arcuate needle passer and includes a first latching feature adapted to releasably secure the arcuate needle to the first arcuate needle passer and a second latching feature adapted to releasably secure the arcuate needle to the second arcuate needle passer.

20 Claims, 10 Drawing Sheets

(56) References Cited

U.S. PATENT DOCUMENTS

| | | |
|---|---|---|
| 6,506,196 B1 | 1/2003 | Laufer |
| 6,554,845 B1 | 4/2003 | Fleenor et al. |
| 6,569,085 B2 | 5/2003 | Kortenbach et al. |
| 6,626,917 B1 | 9/2003 | Craig |
| 6,663,639 B1 | 12/2003 | Laufer et al. |
| 6,719,763 B2 | 4/2004 | Chung et al. |
| 6,740,030 B2 | 5/2004 | Martone et al. |
| 6,746,457 B2 | 6/2004 | Dana et al. |
| 6,755,843 B2 | 6/2004 | Chung et al. |
| 6,773,441 B1 | 8/2004 | Laufer et al. |
| 6,808,491 B2 | 10/2004 | Kortenbach et al. |
| 6,821,285 B2 | 11/2004 | Laufer et al. |
| 6,835,200 B2 | 12/2004 | Laufer et al. |
| 6,908,427 B2 | 6/2005 | Fleener et al. |
| 6,997,931 B2 | 2/2006 | Sauer et al. |
| 7,056,284 B2 | 6/2006 | Martone et al. |
| 7,063,710 B2 | 6/2006 | Takamoto et al. |
| 7,063,715 B2 | 6/2006 | Onuki et al. |
| 7,094,246 B2 | 8/2006 | Anderson et al. |
| 7,144,401 B2 | 12/2006 | Yamamoto et al. |
| 7,147,646 B2 | 12/2006 | Dana et al. |
| 7,153,314 B2 | 12/2006 | Laufer et al. |
| 7,220,266 B2 | 5/2007 | Gambale |
| 7,232,445 B2 | 6/2007 | Kortenbach et al. |
| 7,235,086 B2 | 6/2007 | Sauer et al. |
| 7,326,221 B2 | 2/2008 | Sakamoto et al. |
| 7,344,545 B2 | 3/2008 | Takemoto et al. |
| 7,347,863 B2 | 3/2008 | Rothe et al. |
| 7,361,180 B2 | 4/2008 | Saadat et al. |
| 7,530,985 B2 | 5/2009 | Takemoto et al. |
| 7,601,161 B1 | 10/2009 | Nobles et al. |
| 7,618,425 B2 | 11/2009 | Yamamoto et al. |
| 7,713,277 B2 | 5/2010 | Laufer et al. |
| 7,722,633 B2 | 5/2010 | Laufer et al. |
| 7,727,246 B2 | 6/2010 | Sixto, Jr. et al. |
| 7,736,373 B2 | 6/2010 | Laufer et al. |
| 7,776,057 B2 | 8/2010 | Laufer et al. |
| 7,776,066 B2 | 8/2010 | Onuki et al. |
| 7,842,051 B2 | 11/2010 | Dana et al. |
| 7,846,180 B2 | 12/2010 | Cerier |
| 7,857,823 B2 | 12/2010 | Laufer et al. |
| 7,896,893 B2 | 3/2011 | Laufer et al. |
| 7,918,867 B2 | 4/2011 | Dana et al. |
| 7,951,157 B2 | 5/2011 | Gambale |
| 7,992,571 B2 | 8/2011 | Gross et al. |
| 7,993,368 B2 | 8/2011 | Gambale et al. |
| 8,016,840 B2 | 9/2011 | Takemoto et al. |
| 8,021,376 B2 | 9/2011 | Takemoto et al. |
| 8,057,494 B2 | 11/2011 | Laufer et al. |
| 8,062,314 B2 | 11/2011 | Sixto, Jr. et al. |
| 8,066,721 B2 | 11/2011 | Kortenbach et al. |
| 8,105,355 B2 | 1/2012 | Page et al. |
| 8,211,123 B2 | 7/2012 | Gross et al. |
| 8,216,253 B2 | 7/2012 | Saadat et al. |
| 8,226,667 B2 | 7/2012 | Viola et al. |
| 8,277,468 B2 | 10/2012 | Laufer et al. |
| 8,287,554 B2 | 10/2012 | Cerier et al. |
| 8,287,556 B2 | 10/2012 | Gilkey et al. |
| 8,308,765 B2 | 11/2012 | Saadat et al. |
| 8,313,496 B2 | 11/2012 | Sauer et al. |
| 8,361,089 B2 | 1/2013 | Chu |
| 8,388,632 B2 | 3/2013 | Gambale |
| 8,425,555 B2 | 4/2013 | Page et al. |
| 8,454,631 B2 | 6/2013 | Viola et al. |
| 8,465,506 B2 | 6/2013 | McLawhorn et al. |
| 8,480,691 B2 | 7/2013 | Dana et al. |
| 8,540,735 B2 | 9/2013 | Mitelberg et al. |
| 8,551,120 B2 | 10/2013 | Gambale |
| 8,585,720 B2 | 11/2013 | Gross et al. |
| 8,632,553 B2 | 1/2014 | Sakamoto et al. |
| 8,641,728 B2 | 2/2014 | Stokes et al. |
| 8,679,136 B2 | 3/2014 | Mitelberg |
| 8,709,022 B2 | 4/2014 | Stone et al. |
| 8,764,771 B2 | 7/2014 | Chu |
| 8,882,785 B2 | 11/2014 | DiCesare et al. |
| 8,926,634 B2 | 1/2015 | Rothe et al. |
| 8,992,570 B2 | 3/2015 | Gambale et al. |
| 9,011,466 B2 | 4/2015 | Adams et al. |
| 9,072,480 B2 * | 7/2015 | Hart ............ A61B 17/0625 |
| 9,089,325 B2 | 7/2015 | Mitelberg et al. |
| 9,125,646 B2 | 9/2015 | Woodard, Jr. et al. |
| 9,198,562 B2 | 12/2015 | Mitelberg et al. |
| 9,320,515 B2 | 4/2016 | Dana et al. |
| 9,486,126 B2 | 11/2016 | West et al. |
| 9,504,465 B2 | 11/2016 | Chu |
| 9,510,817 B2 | 11/2016 | Saadat et al. |
| 9,549,728 B2 | 1/2017 | Chu |
| 9,750,494 B2 | 9/2017 | Gross et al. |
| 9,788,831 B2 | 10/2017 | Mitelberg |
| 9,844,366 B2 | 12/2017 | Woodard, Jr. et al. |
| 9,867,610 B2 | 1/2018 | Mitelberg et al. |
| 10,045,871 B2 | 8/2018 | Saadat et al. |
| 10,143,463 B2 | 12/2018 | Dana et al. |
| 10,194,902 B2 | 2/2019 | Nobles et al. |
| 10,335,142 B2 | 7/2019 | Raybin et al. |
| 2002/0107530 A1 | 8/2002 | Sauer et al. |
| 2003/0181924 A1 | 9/2003 | Yamamoto et al. |
| 2003/0195529 A1 | 10/2003 | Takamoto et al. |
| 2003/0204205 A1 | 10/2003 | Sauer et al. |
| 2004/0002699 A1 | 1/2004 | Ryan et al. |
| 2004/0138706 A1 | 7/2004 | Abrams et al. |
| 2005/0033319 A1 | 2/2005 | Gambale et al. |
| 2005/0250985 A1 | 11/2005 | Saadat et al. |
| 2006/0030868 A1 | 2/2006 | Bennett, III |
| 2006/0282094 A1 | 12/2006 | Stokes et al. |
| 2007/0270908 A1 | 11/2007 | Stokes et al. |
| 2008/0086148 A1 | 4/2008 | Baker et al. |
| 2009/0177031 A1 | 7/2009 | Surti et al. |
| 2010/0016870 A1 | 1/2010 | Campbell |
| 2010/0137681 A1 | 6/2010 | Ewers et al. |
| 2010/0198006 A1 | 8/2010 | Greenburg et al. |
| 2011/0152891 A1 * | 6/2011 | McLawhorn ...... A61B 17/0625 606/144 |
| 2011/0276064 A1 | 11/2011 | Henrichsen et al. |
| 2012/0158023 A1 | 6/2012 | Miltelberg et al. |
| 2012/0271327 A1 | 10/2012 | West et al. |
| 2012/0277768 A1 | 11/2012 | Viola et al. |
| 2013/0046335 A1 * | 2/2013 | Deutsch ............ A61B 17/0625 606/205 |
| 2013/0096581 A1 | 4/2013 | Gilkey et al. |
| 2013/0304093 A1 | 11/2013 | Serina et al. |
| 2014/0121457 A1 | 5/2014 | Mort et al. |
| 2014/0128668 A1 | 5/2014 | Cox et al. |
| 2015/0126983 A1 | 5/2015 | Alvarado et al. |
| 2016/0045197 A1 | 2/2016 | Mitelberg et al. |
| 2017/0035413 A1 | 2/2017 | Takahashi |
| 2017/0042534 A1 | 2/2017 | Nobles et al. |
| 2017/0086817 A1 | 3/2017 | Mitelberg |
| 2017/0086818 A1 | 3/2017 | Mitelberg |
| 2017/0119371 A1 | 5/2017 | Mims et al. |
| 2017/0319197 A1 | 11/2017 | Gross et al. |
| 2018/0042602 A1 | 2/2018 | Mitelberg et al. |
| 2018/0042603 A1 | 2/2018 | Mitelberg et al. |
| 2018/0153381 A1 | 6/2018 | Wei et al. |
| 2018/0221009 A1 | 8/2018 | Mitelberg et al. |
| 2018/0235604 A1 | 8/2018 | Comee et al. |
| 2018/0344501 A1 | 12/2018 | Saadat et al. |

FOREIGN PATENT DOCUMENTS

| | | |
|---|---|---|
| EP | 1354558 A2 | 10/2003 |
| EP | 1520509 A1 | 4/2005 |
| EP | 2108304 A2 | 10/2009 |
| EP | 2515767 A1 | 7/2011 |
| JP | 2003305046 A | 10/2003 |
| JP | 2013-514866 A | 5/2013 |
| WO | 0101868 A1 | 1/2001 |
| WO | 0189393 A1 | 11/2001 |
| WO | 2008016592 A2 | 2/2008 |
| WO | 2008045376 A2 | 4/2008 |
| WO | 2008098124 A1 | 8/2008 |
| WO | 2010036227 A1 | 4/2010 |
| WO | 2010085793 | 7/2010 |
| WO | 2013022959 A2 | 2/2013 |

(56) References Cited

FOREIGN PATENT DOCUMENTS

| WO | 2016200811 A1 | 12/2016 |
| WO | 2017087856 A1 | 5/2017 |
| WO | 2018156603 A1 | 8/2018 |

OTHER PUBLICATIONS

International Search Report and Written Opinion dated Oct. 1, 2019 for International Application No. PCT/US2019/038006.
Invitation to Pay Additional Fees dated Sep. 26, 2019 for International Application No. PCT/US2019/037995.
International Search Report and Written Opinion dated Dec. 6, 2019 for International Application No. PCT/US2019/037995.
International Search Report and Written Opinion dated Nov. 18, 2019 for International Application No. PCT/US2019/049774.
International Search Report and Written Opinion dated Sep. 20, 2019 for International Application No. PCT/US2019/039312.
International Search Report and Written Opinion dated Jun. 17, 2021 for International Application No. PCT/US2021/024855.
Korean Intellectual Property Office, Office Action, KR Application No. 10-2019-7027516, Mar. 29, 2021 (11 pgs).
International Search Report and Written Opinion dated May 22, 2018 for International Application No. PCT/US2018/018982.

\* cited by examiner

SUTURE BASED CLOSURE DEVICE

CROSS REFERENCE TO RELATED APPLICATIONS

The present application claims the benefit of and priority to U.S. Provisional Patent Application Ser. No. 63/002,822, filed on Mar. 31, 2020, the disclosure of which is incorporated herein by reference.

TECHNICAL FIELD

The disclosure is directed to devices for suturing tissue and more particularly to devices that work with an endoscope or similar device for endoscopically suturing tissue.

BACKGROUND

A variety of endoscopic treatments may result in defects (or wounds) that are too large for hemostasis clips to easily bridge and thus help to close the defect. Examples of such endoscopic treatments include removal of large lesions, tunneling under the mucosal layer, full thickness removal of tissue, treating other organs by passing outside of the gastrointestinal tract, and repair of post-surgical issues such as post-surgical leaks, failing surgical staple lines and anastomotic leaks. Endoscopic treatments also include bariatric revision procedures. Of the known devices and methods for endoscopically closing large defects, each has certain advantages and disadvantages.

SUMMARY

The disclosure is directed to several alternative designs, materials and methods of devices for endoscopically closing large defects. In an example, a suture device includes a mounting structure that is adapted to be secured relative to a distal end of an endoscope and a suture ring that is secured relative to the mounting structure and defines an arcuate channel extending within the suture ring. A first arcuate needle passer is slidingly disposed within a first side of the arcuate channel and includes a working end and a control end. A first control element is operably coupled to the control end of the first arcuate needle passer and an arcuate needle is releasably securable to the first needle passer.

Alternatively or additionally, the suture device may further include a second arcuate needle passer that is slidingly disposed within a second side of the arcuate channel and that includes a working end and a control end. A second control element is operably coupled to the control end of the second arcuate needle passer. The arcuate needle is passable between the first arcuate needle passer and the second arcuate needle passer and includes a first latching feature adapted to releasably secure the arcuate needle to the first arcuate needle passer and a second latching feature adapted to releasably secure the arcuate needle to the second arcuate needle passer. The first control element and the second control element cross over each other upon entering the arcuate channel of the suture ring.

Alternatively or additionally, the first latching feature may include a first pair of radially spaced protrusions disposed within a first portion of the arcuate needle and the second latching feature may include a second pair of radially spaced protrusions disposed within a second portion of the arcuate needle.

Alternatively or additionally, the arcuate needle may further include a suture aperture disposed between the first latching feature and the second latching feature.

Alternatively or additionally, the first needle passer may include a first aperture that is complementary to a first protrusion of the first pair of protrusions and a second aperture that is complementary to a second protrusion of the first pair of protrusions.

Alternatively or additionally, the first arcuate needle passer may include a first pair of longitudinally aligned slots extending from the working end and towards the control end of the first arcuate needle passer, each of the first pair of longitudinally aligned slots extending through one of the first aperture and the second aperture such that the first arcuate needle passer is able to flex relative to the first aperture and the second aperture when not constrained by the first side of the arcuate suture ring.

Alternatively or additionally, the second arcuate needle passer may include a first aperture that is complementary to a first protrusion of the second pair of protrusions and a second aperture that is complementary to a second protrusion of the second pair of protrusions.

Alternatively or additionally, the second arcuate needle passer may include a second pair of longitudinally aligned slots extending from the working end and towards the control end of the second arcuate needle passer, each of the second pair of longitudinally aligned slots extending through one of the first aperture and the second aperture such that the second arcuate needle passer is able to flex relative to the first aperture and the second aperture when not constrained by the second side of the arcuate suture ring.

Alternatively or additionally, the suture ring may extend in a circle from a first open end to a second open end, the first open end and the second open end spaced apart a distance that permits tissue to extend therebetween.

Alternatively or additionally, the annular channel may have a circular cross-sectional profile except for a first region proximate the first open end and a second region proximate the second open end.

Alternatively or additionally, the first region and the second region may each have an ovoid cross-sectional profile that allows the first arcuate needle passer and/or the second needle passer to begin to flex as the first arcuate needle passer exits the first open end and/or the second arcuate needle passer exits the second open end.

Alternatively or additionally, the first control element may enter the first side of the arcuate channel substantially parallel to a tangent of the first arcuate needle passer proximate where the first control element is secured to the first arcuate needle passer.

Alternatively or additionally, the second control element may enter the second side of the arcuate channel substantially parallel to a tangent of the second arcuate needle passer proximate where the second control element is secured to the second arcuate needle passer.

Alternatively or additionally, the suture device may further include a first tubular member housing the first control element and a second tubular member housing the second control element.

In another example, a suture device that is adapted to be used in combination with an endoscope includes a suture ring having a first side and a second side and defining an arcuate channel extending within the suture ring. A first tubular member includes a curved distal portion that curves in a direction opposed to a direction of curvature of the first side of the suture ring. A second tubular member includes a curved distal portion that curves in a direction opposed to a direction of curvature of the second side of the suture ring. A first arcuate needle passer is slidingly disposed within a first side of the arcuate channel and a second arcuate needle passer is slidingly disposed within a second side of the arcuate channel. A first control element is disposed within the first tubular member and is operably coupled to the first arcuate needle passer. A second control element is disposed within the second tubular member and is operably coupled to the second arcuate needle passer. An arcuate needle is passable between the first arcuate needle passer and the second arcuate needle passer by manipulating the first control element and the second control element.

Alternatively or additionally, the first needle passer may include a working end adapted to releasably secure the arcuate needle.

Alternatively or additionally, the first arcuate needle passer may include a first pair of longitudinally aligned slots extending through the working end of the first needle passer such that the working end of the first needle passer is able to flex when not constrained by the first side of the arcuate suture ring.

Alternatively or additionally, the second arcuate needle passer includes a working end adapted to releasably secure the arcuate needle.

Alternatively or additionally, the second arcuate needle passer may include a second pair of longitudinally aligned slots extending through the working end of the second arcuate needle passer such that the working end of the second arcuate needle passer is able to flex when not constrained by the second side of the arcuate suture ring.

In another example, a suture device that is adapted to be used in combination with an endoscope includes an end cap ring that is adapted to be secured to a distal end of an endoscope and a C-shaped suture ring that is secured to the end cap ring. The C-shaped suture ring has a first side and a second side, and defines an arcuate channel extending within the suture ring. A first arcuate needle passer is slidingly disposed within a first side of the arcuate channel and a second arcuate needle passer is slidingly disposed within a second side of the arcuate channel. A first control element is adapted to enter the first side of the arcuate channel substantially parallel to a tangent of the first needle passer proximate where the first control element is secured to the first needle passer and a second control element is adapted to enter the second side of the arcuate channel substantially parallel to a tangent of the second needle passer proximate where the second control element is secured to the second needle passer. An arcuate needle is passable between the first arcuate needle passer and the second arcuate needle passer by manipulating the first control element and the second control element.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
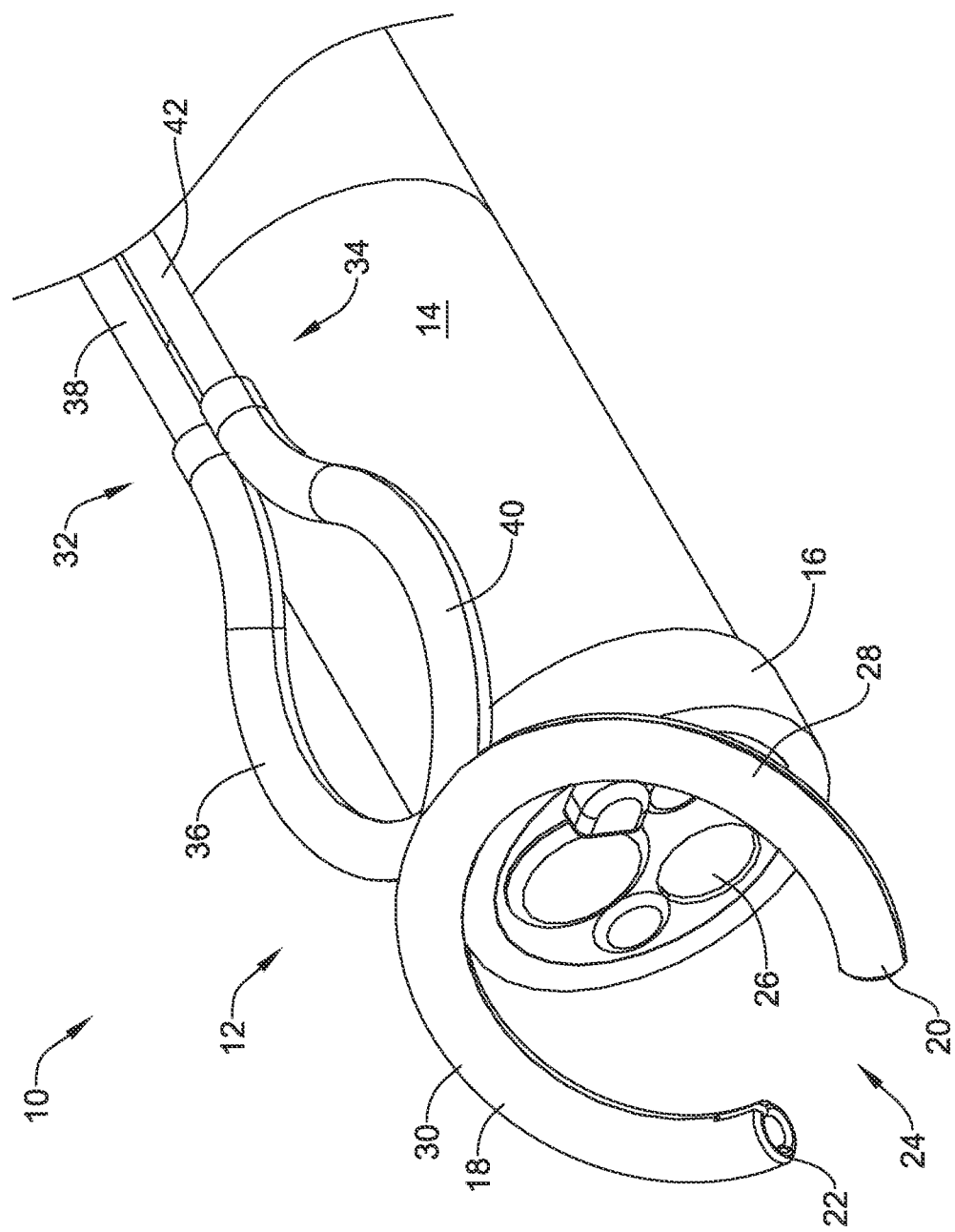
FIG. 1 is a perspective view of an illustrative assembly including an illustrative suture device secured relative to an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to devices that are configured to be used in combination with an endoscope or a similar delivery device for closing wounds within the body. In some instances, the suture devices described herein may be configured such that they may be used in combination with a single working channel endoscope or a dual working channel endoscope within a single working or available channel of an endoscope, and in some cases may be operated by a single individual, although in some cases a second individual may be involved.

Figure 2:
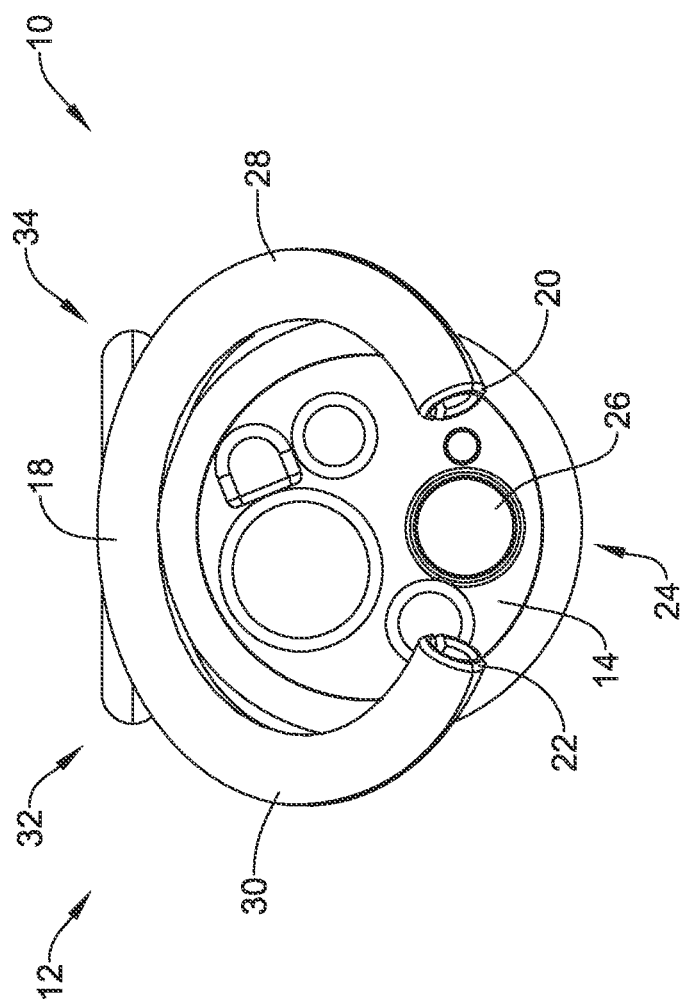
FIG. 2 is an end view of the illustrative assembly of FIG. 1.

FIG. 1 is a perspective view of an illustrative assembly 10 that includes an illustrative suture device 12 secured relative to an endoscope 14 while FIG. 2 is an end view of the illustrative assembly 10. As shown, the illustrative suture device 12 includes an end cap ring 16 that is configured to secure the suture device 12 relative to the endoscope 14. For example, the end cap ring 16 may be any over-the-scope connector. In some instances, the suture device 12 may instead include other structures or features (not illustrated) that are adapted to secure the suture device 12 relative to the endoscope 14. The suture device 12 includes a C-shaped suture ring 18. As will be shown with respect to subsequent drawings, the C-shaped suture ring 18 is adapted to permit arcuate-shaped needle passers to slide within the C-shaped suture ring 18 in order to pass an arcuate needle (not shown in FIG. 1) to pass back and forth between a pair of arcuate-shaped needle passers.

The C-shaped suture ring 18 may be considered as tracing out a circle, apart from a missing part of the circle as shown between a first open end 20 and a second open end 22. The missing part of the circle may be considered as defining a region 24 that can accommodate tissue therein to be sutured. In some instances, the relative dimensions of the C-shaped suture ring 18, including the relative distance between the first open end 20 and the second open end 22 may be varied in order to accommodate different tissues, different relative needle passer sizes, and the like. Additionally, as shown the C-shaped suture ring 18 may be considered as forming a particular arcuate angle relative to the end cap ring 16. This is merely illustrative, as the C-shaped suture ring 18 may be disposed at any desired angle relative to the end cap ring 16. The C-shaped suture ring 18 may be attached at any desired position relative to the end cap 16. In some cases, the relative position of the C-shaped suture ring 18 may be adjusted after delivery. In some cases, as best seen in FIG. 2, the suture device 12 may be secured relative to the endoscope 14 such that the region 24 is centered or at least substantially centered relative to a main working channel 26 of the endoscope 14, although this is not required in all cases. While additional tools are not necessary for usage of the suture device 12, in some cases there may be a desire to provide tools through the working channel 26 that can reach the region 24. For example, there may be a desire to use a grasper to help pull tissue towards the region 24, or to hold tissue relative to the region 24, while suturing. The region 24 may, therefore, also be considered as a working space for the suture device 12.

The C-shaped suture ring 18 may be considered as including a first side 28 and a second side 30. The suture device 12 includes a first tubular member 32 and a second tubular member 34. The first side 28 of the C-shaped suture ring 18 is to the right (in the illustrated orientation) and the second side 30 of the C-shaped suture ring is to the left while the first tubular member 32 is to the left and the second tubular member 34 is to the right (e.g. see FIG. 3, in which first and second control elements are visible. The first tubular member 32 may be seen as including a curved portion 36 and a linear portion 38 that extends proximally. Similarly, the second tubular member 34 may be seen as including a curved portion 40 and a linear portion 42 that extends proximally. It will be appreciated that the curved portion 36 of the first tubular member 32 is curved in a direction that is opposite a direction in which the first side 28 of the C-shaped suture ring 18 curves, and that the curved portion 40 of the second tubular member 34 is curved in a direction that is opposite a direction in which the second side 30 of the C-shaped suture ring 18 curves. In some cases, the relative curvature of the sides of the C-shaped suture ring 18 and the first and second tubular member 32, 34 help to align the control elements with the arcuate needle passers (not shown in FIGS. 1 and 2).

FIGS. 3 through 6 are partial cutaway views of the suture device 12 in which a portion of the suture ring 12, the curved portion 36 of the first tubular member 32 and the curved portion 40 of the second tubular member 34 are cutaway to reveal further details of the suture device 12. The suture device 12 includes a first arcuate needle passer 44 that is operably coupled with a first control element 46 and a second arcuate needle passer 48 that is operably coupled with a second control element 50. It will be appreciated that the control elements 46, 50 cross over each other at a location 52 proximate to where the first control element 46 is secured to the first arcuate needle passer 44 and the second control element 50 is secured to the second arcuate needle passer 48. In some cases, allowing the first control element 46 and the second control element 50 to cross over each other can result in reduced effort needed to move the first control element 46 and the second control element 50 as a result of the control elements 46, 50 being better aligned with their corresponding arcuate needle passers 44, 48. While the second control element 50 is shown as passing over the first control element 46, this is just an example. An arcuate needle 54 may be seen as being passed between the first arcuate needle passer 44 and the second arcuate needle passer 48.

In some cases, the first control element 46 enters the first side 28 of the arcuate channel 56 of the C-shaped suture ring 18 in a direction that is substantially parallel to a tangent of the first arcuate needle passer 44 proximate to where the first control element 46 is secured to the first arcuate needle passer 44. In some cases, the second control element 50 enters the second side 30 of the arcuate channel 56 of the C-shaped suture ring 18 in a direction that is substantially parallel to a tangent of the second arcuate needle passer 48 proximate to where the second control element 50 is secured to the second arcuate needle passer 48.

The C-shaped suture ring 18 defines an arcuate channel 56 that extends through the C-shaped suture ring 18 from the first open end 20 to the second open end 22. As will be discussed in greater detail with respect to FIGS. 8 and 9, the arcuate channel 56 has a constant inner diameter and inner cross-sectional profile that is about the same as an outer diameter and outer cross-sectional profile of each of the first arcuate needle passer 44 and the second arcuate needle passer 48 with the exception of a first region 58 that is proximate the first open end 20 and a second region 60 that is proximate the second open end 22. In some cases, as illustrated, the first region 58 includes a slot 62 that accommodates a suture secured to the arcuate needle 54 when the arcuate needle 54 is positioned therein and the second region 60 includes a slot 64 that accommodates a suture secured to the arcuate needle 54 when the arcuate needle 54 is positioned therein While no proximal handle or other mechanism is shown, it will be appreciated that a user can selectively advance the first arcuate needle passer 44 by actuating the first control element 46 in a first direction and can selectively retract the first arcuate needle passer 44 by actuating the first control element 46 in a second, opposing direction. A user can selectively advance the second arcuate needle passer 48 by actuating the second control element 50 in a first direction and can selectively retract the second arcuate needle passer 48 by actuating the second control element 50 in a second, opposing direction. A user may also hold either the first arcuate needle passer 44 or the second arcuate needle passer 48 in a particular position by simply holding the appropriate control element 46, 50 from moving.

Figure 3:
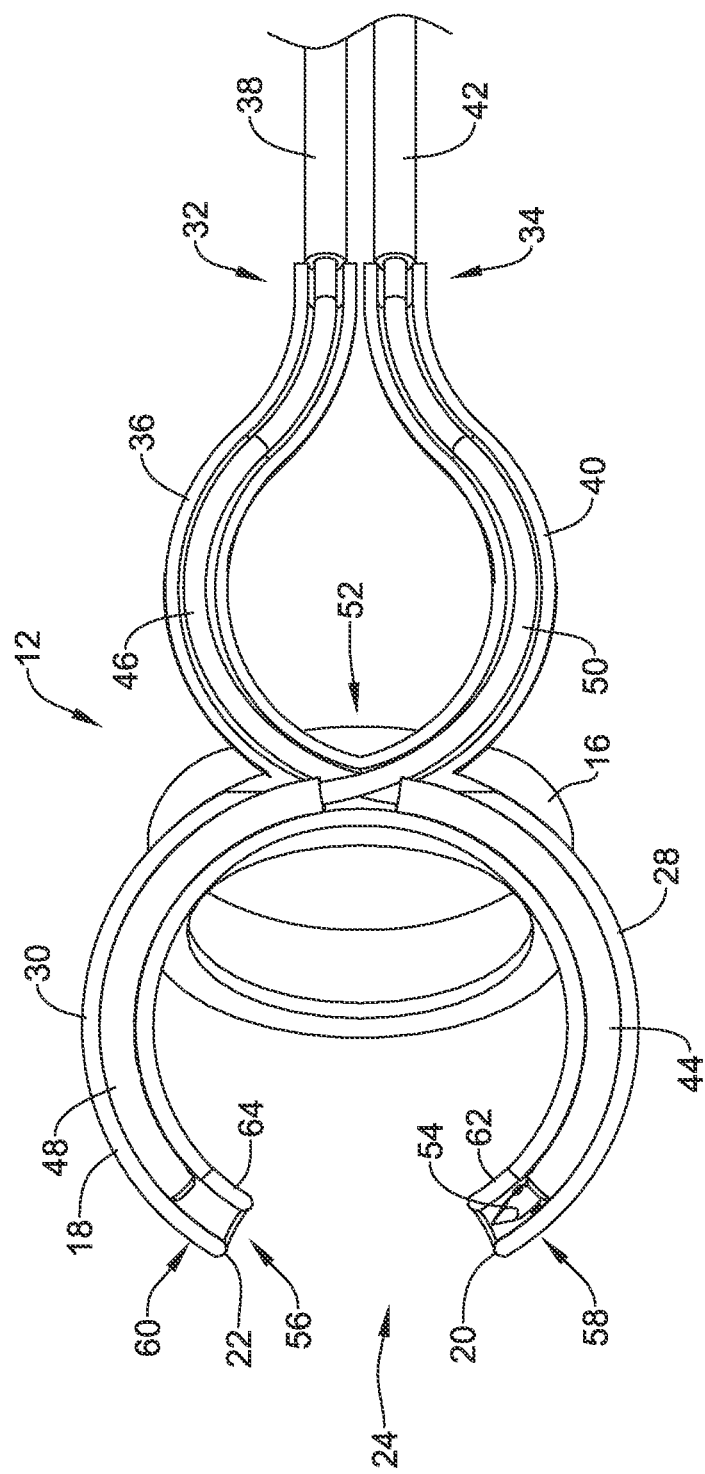
FIGS. 3 through 6 are partial-cutaway views of the illustrative suture device of FIG. 1, showing step by step how an arcuate needle is passed from a first arcuate needle passer to a second arcuate needle passer.
Figure 4:
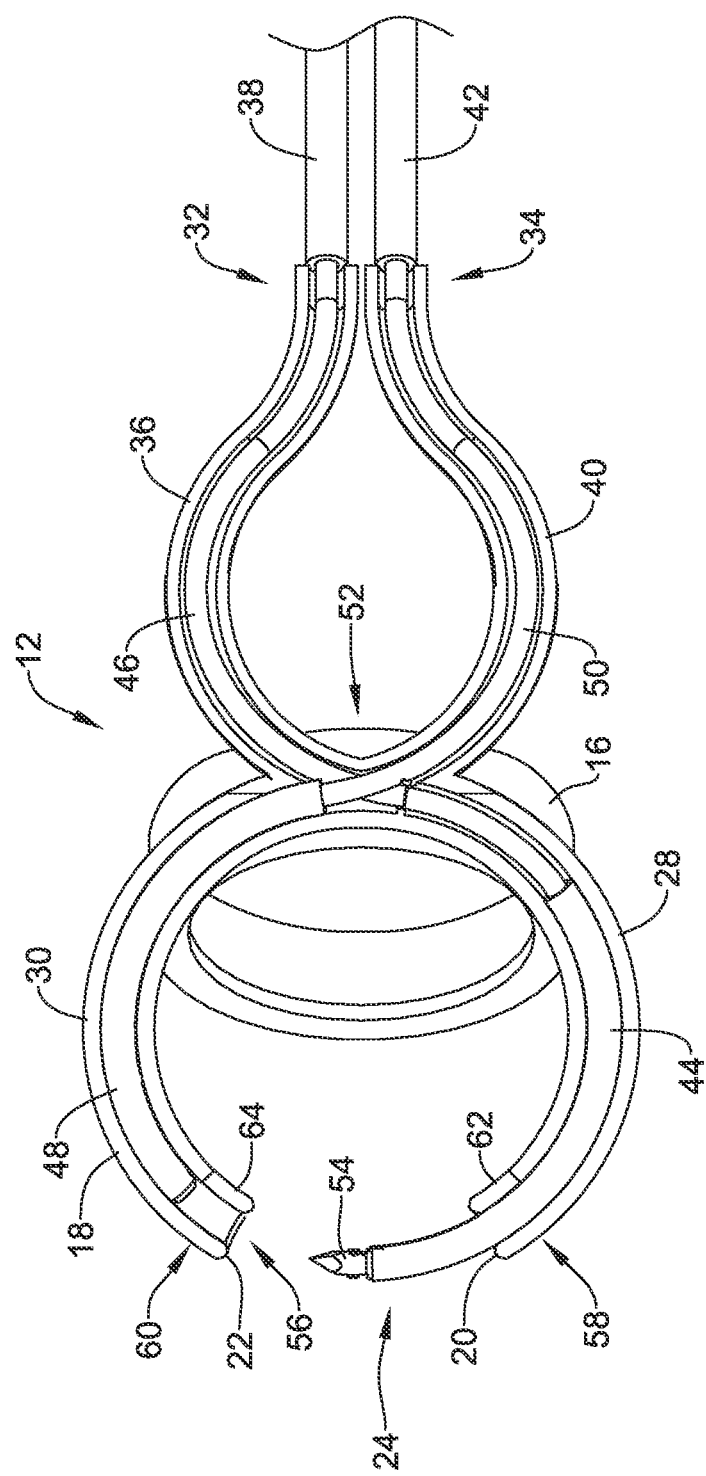
Figure 5:
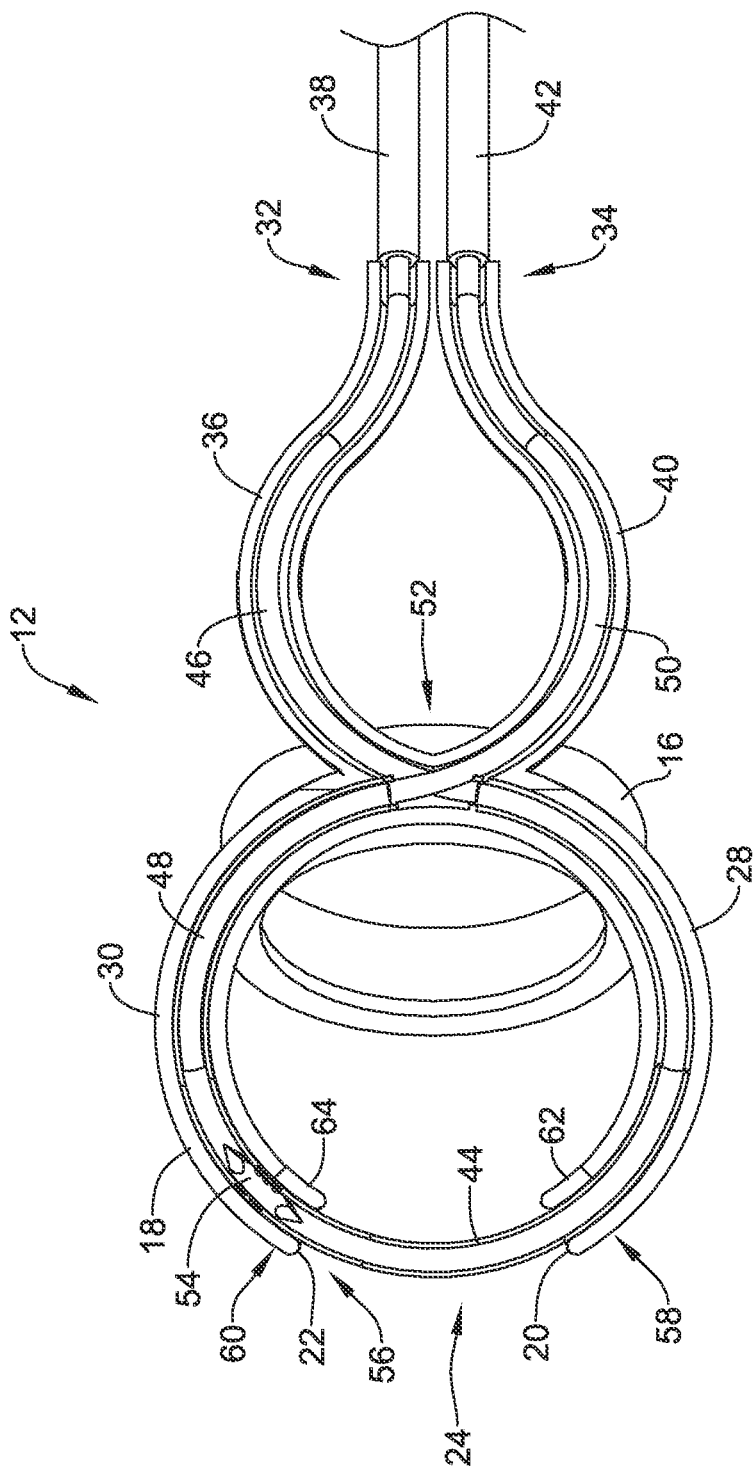
Figure 6:
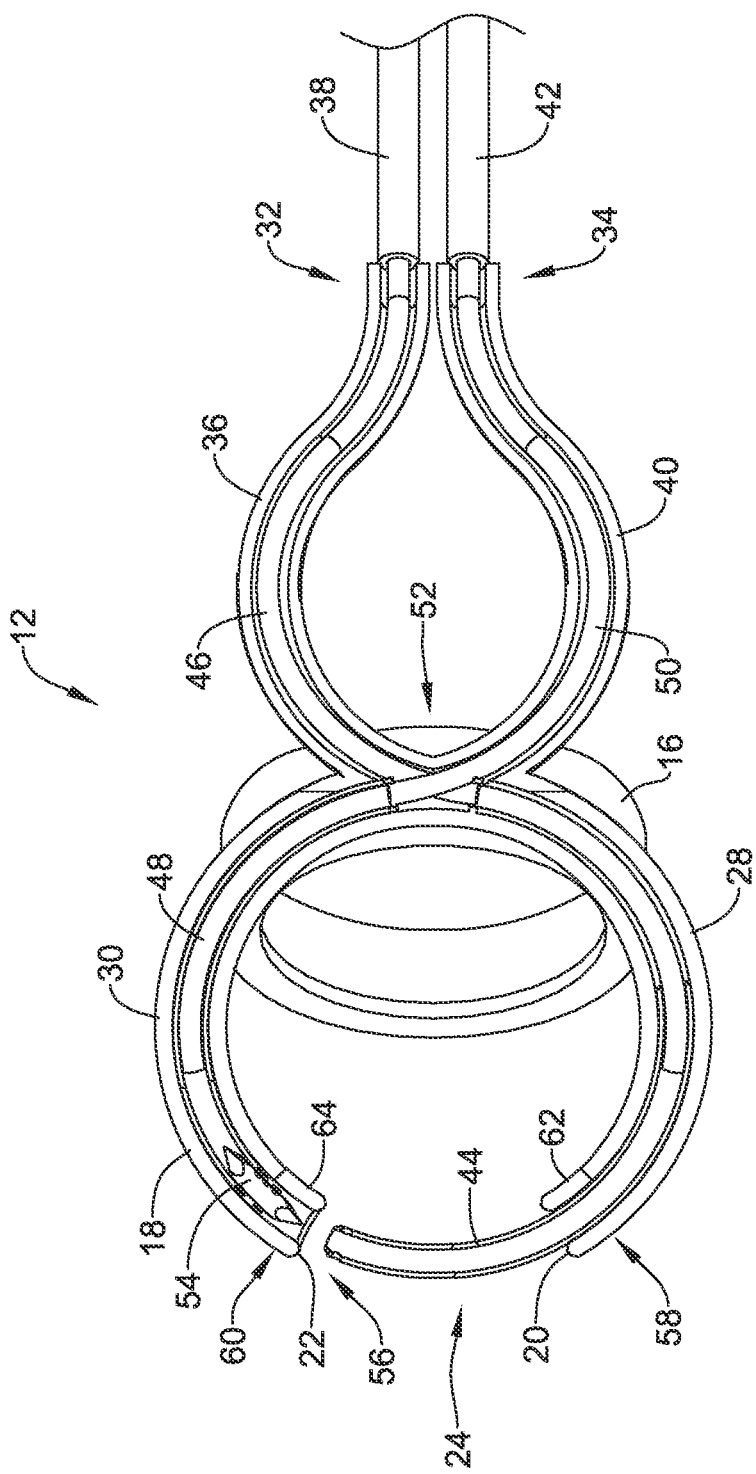

Starting with FIG. 3, the first arcuate needle passer 44 can be seen as being retracted into the first side 28 of the C-shaped suture ring 18 and the second arcuate needle passer 48 can be seen as being retracted into the second side 30 of the C-shaped suture ring 18. The arcuate needle 54 can be seen as being secured to the first arcuate needle passer 44. Additional details as to how the arcuate needle 54 is secured to the first arcuate needle passer 44 will be discussed subsequently with respect to FIGS. 7 and 8. Moving to FIG. 4, it can be seen that the first arcuate needle passer 44 has been advanced partially out of the first side 28 of the C-shaped suture ring 18 and into the region 24 by advancing the first control element 46 in an appropriate direction. Continuing on to FIG. 5, the first arcuate needle passer 44 has been advanced further such that the arcuate needle 54 has contacted the second arcuate needle passer 48. In some cases, the second arcuate needle passer 48 may be held in place by holding the second control element 50 in position while the first arcuate needle passer 44 is advanced further to drive the arcuate needle 54 into the second arcuate needle passer 48. Finally, in FIG. 6, the arcuate needle 54 may be seen as being secured to the second arcuate needle 48, as the first arcuate needle passer 44 has been withdrawn by moving the first control element 46 in an appropriate direction.

It will be appreciated that the steps shown in FIGS. 3 through 6 will result in having placed a stitch through tissue present within the region or working area 24. By moving the suture device 12 (secured to the distal end of the endoscope 14) laterally, a subsequent stitch may be placed by reversing the steps shown in FIGS. 3 through 6. As noted, in some cases, a grasper or other tool may be provided through the working channel 16 of the endoscope 14, although this is not required for operation of the suture device 12.

Figure 7:
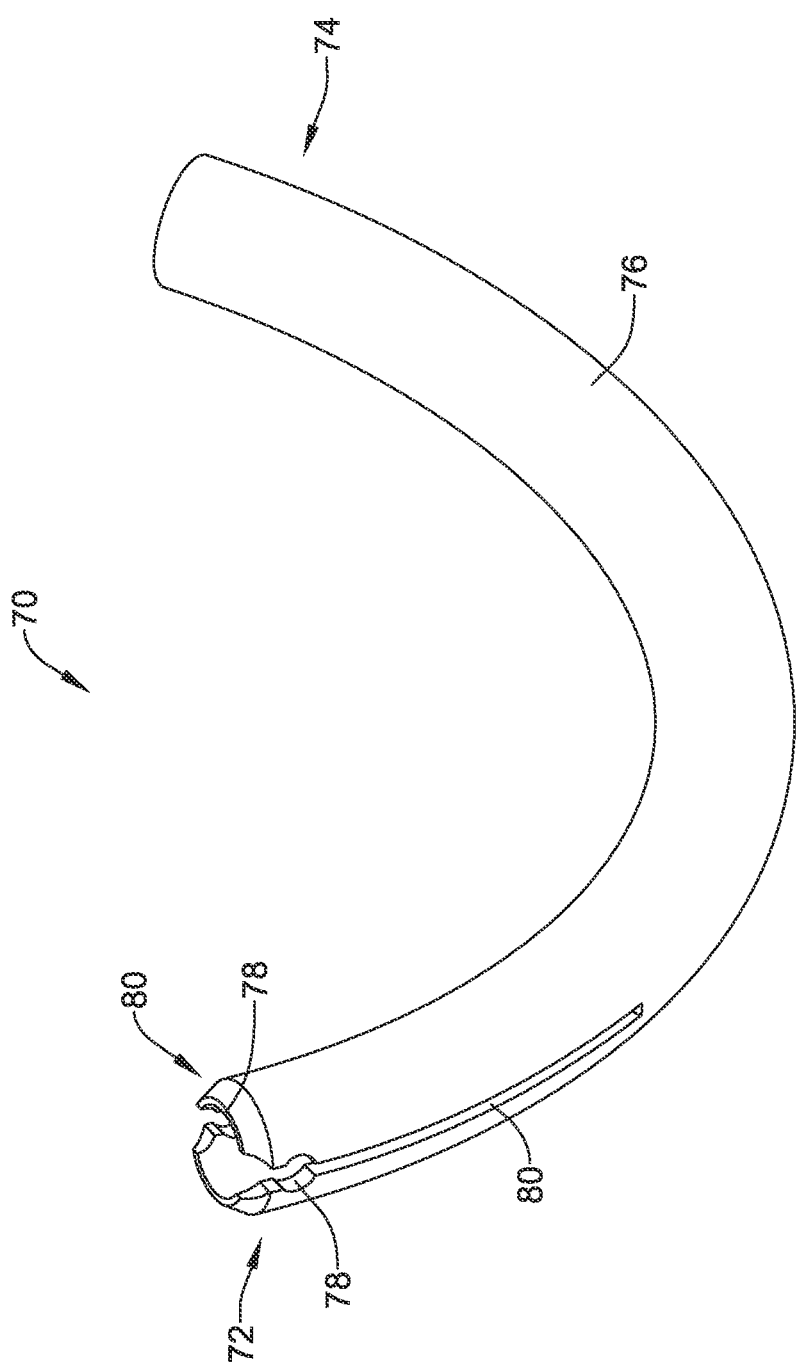
FIG. 7 is a perspective view of an arcuate needle passer that is usable in the illustrative assembly of FIG. 1 as either the first arcuate needle passer or the second arcuate needle passer.

FIG. 7 is a perspective view of an arcuate needle passer 70 that may, for example, be used as either the first arcuate needle passer 44 or the second arcuate needle passer 48. The arcuate needle passer 70 has a curvature that matches the curvature of the C-shaped suture ring 18 such that the arcuate needle passer 70 may easily slide relative to the arcuate channel 56 within the C-shaped suture ring 18. While the arcuate needle passer 70 is shown as having a circular cross-sectional shape, this is not required in all cases. For example, the arcuate needle passer 70 could have a non-circular cross-sectional shape such as square or rectangular. The arcuate needle passer 70 may be considered as having a working end 72 and a control end 74. The working end 72 is adapted to releasably secure the arcuate needle 54 while the control end 74 is adapted to be secured to a control element such as the first control element 46 or the second control element 50. The arcuate needle passer 70 has a body 76 that extends from the working end 72 to the control end 74. In some cases, the body 76 is formed from a hypotube, and thus is hollow.

The working end 72 includes a pair of apertures 78 that are radially spaced about 180 degrees apart. As will be discussed, the apertures 78 may be adapted to releasably secure corresponding and complementary latching features present on the arcuate needle 54. The arcuate needle passer 70 includes a pair of slots 80 that may also be radially spaced about 180 degrees apart such that each of the slots 80 passes through one of the apertures 78. When the arcuate needle passer 70 is positioned within the arcuate channel 56 of the C-shaped suture ring 18, it will be appreciated that the relative dimensions therebetween limit movement and thus secure the arcuate needle 54 relative to the arcuate needle passer 70. When the working end 72 extends outwardly from the arcuate channel 56 of the C-shaped suture ring 18, the slots 80 are adapted to allow the working end 72 to fully flex relative to the apertures 78, which can allow the arcuate needle passer 70 to release the arcuate needle 54.

Figure 8:
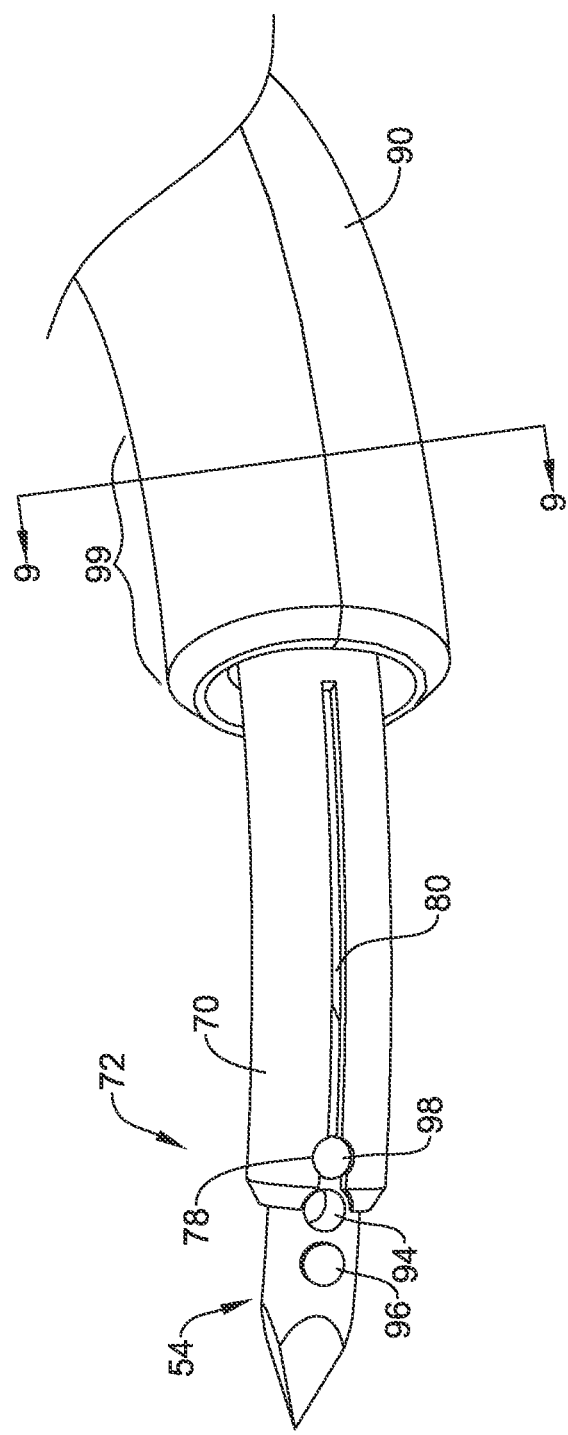
FIG. 8 is a perspective view of a portion of the illustrative suture device of FIG. 1, showing a portion of the suture ring, an arcuate needle passer and the arcuate needle secured relative to the arcuate needle passer.
Figure 9:
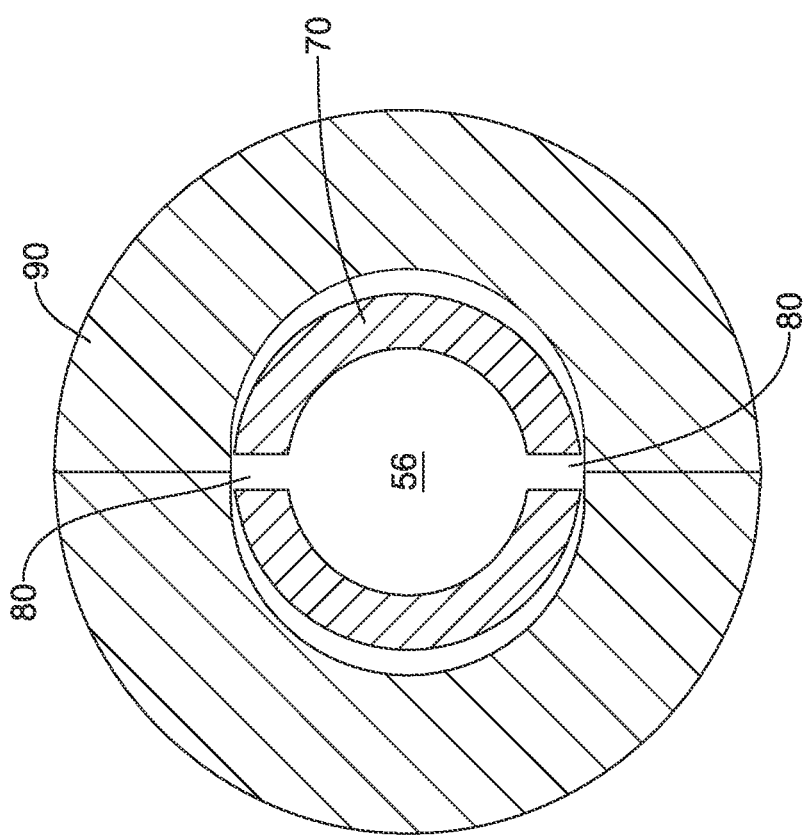
FIG. 9 is a cross-sectional view of the portion of the illustrative suture device shown in FIG. 8, taken along the line 9-9 of FIG. 8.

FIG. 8 is a perspective view showing a portion 90 of the C-shaped suture ring 18, the arcuate needle passer 70 and the arcuate needle 54. The portion 90 of the C-shaped suture ring 18 includes a region 99 that corresponds to the first region 58 and/or the second region 60, having a non-circular cross-sectional profile as seen in FIG. 9, which is a cross-section taken along line 9-9 of FIG. 8. One of the slots 80 may be seen as extending through one of the apertures 78, although the other slot 80 and the other aperture 78 are on the opposing side and thus are not visible in this view. The arcuate needle 54 includes a protrusion 98 that engages the visible aperture 78. It will be appreciated that there is a second protrusion 98 that is radially spaced about 180 degrees apart and thus may be engaged in the other aperture 78. As seen in FIG. 9, the inner profile of the region 99 is larger than an outer profile of the arcuate needle passer 70, which permits sufficient flexing of the working end 72 of the arcuate needle passer 70 when the working end 72 is disposed within the region 99 to allow the arcuate needle 54 to be pushed into registration with the working end 72 to permit the arcuate needle 54 to be transferred from one arcuate needle passer to the other. In the position shown in FIG. 8, the arcuate needle passer 70 is positioned to transfer the arcuate needle 54 to another arcuate needle passer.

It will be appreciated that the arcuate needle 54 is always held by at least one of the first arcuate needle passer 44 and the second arcuate needle passer 48. When the working end 72 of the arcuate needle passer 70 (representative of either the first arcuate needle passer 44 or the second arcuate needle passer 48) is disposed within the region 99 (shown in FIG. 8), there is enough flex within the arcuate needle passer 70 to allow the arcuate needle 54 to be transferred from the other arcuate needle passer. When the working end 72 of the arcuate needle passer 70 passes out beyond the region 99, there is enough flex possible relative to the apertures 78 and the slots 80 to permit the arcuate needle passer 70 to transfer the arcuate needle 54 to the other arcuate needle passer. Accordingly, the arcuate needle 54 cannot be dropped as the arcuate needle 54 will always be secured relative to one of the arcuate needle passers 44, 48.

Figure 10:
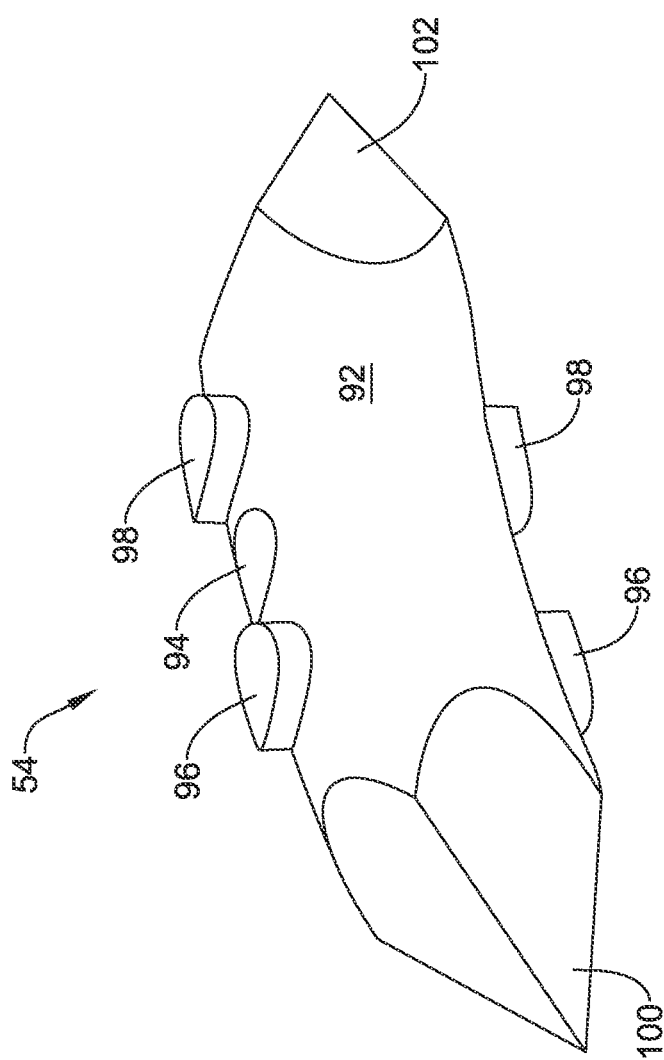
FIG. 10 is a perspective view of the arcuate needle useable in the illustrative suture device of FIG. 1.

FIG. 10 is a perspective view of the arcuate needle 54. The arcuate needle 54 includes a curved body 92 that has a curvature that matches the curvature of the first arcuate needle passer 44 and the second arcuate needle passer 48 such that the first and second arcuate needle passers 44, 48 may move freely within the arcuate channel 56, in response to relative movement of the control elements 46, 50, with the arcuate needle 54 secured to either of the first and second arcuate needle passers 44, 48. The curved body 92 has a pair of protrusions 96 that may be considered as being latching features that can releasably engage corresponding apertures 78 in one of the first and second arcuate needle passers 44, 48. The curved body 92 has a pair of protrusions 98 that may be considered as being latching features that can releasably engage corresponding apertures 78 in the other of the first and second arcuate needle passers 44, 48. While the protrusions 96, 98 are shown as being circular in cross-section, other shapes are contemplated as well. The apertures 78 may vary, depending on the profile of the protrusions 96,98. A suture aperture 94 extends through the curved body 92 to accommodate a suture. The curved body 92 has sharpened ends 100, 102 such that the arcuate needle 54 can pass through tissue in either direction.

It will be appreciated that a variety of different materials may be used in forming the devices described herein. In some cases, a variety of different metals may be used. Illustrative but non-limiting examples of suitable metals include titanium, stainless steel, magnesium, cobalt chromium and others. In some cases, the first control element 46 and the second control element may be made of Nitinol. In some embodiments, for example, the devices described herein may include any suitable polymeric material, including biocompatible materials such as polyurethane or silicone. Suitable polymers include PEEK (polyetheretherketone) and Polycarbonate. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A suture device comprising:
    a mounting structure adapted to be secured relative to a distal end of an endoscope;
    a suture ring secured relative to the mounting structure, the suture ring defining an arcuate channel extending within the suture ring;
    a first arcuate needle passer slidingly disposed within a first side of the arcuate channel, the first arcuate needle pass including a working end and a control end;
    a second arcuate needle passer slidingly disposed within a second side of the arcuate channel, the second arcuate needle passer including a working end and a control end;
    a first control element operably coupled to the control end of the first arcuate needle passer;
    a second control element operably coupled to the control end of the second arcuate needle passer;
    wherein the first control element and the second control element cross over each other upon entering the arcuate channel of the suture ring; and
    an arcuate needle releasably securable to the first arcuate needle passer.

2. The suture device of claim 1, wherein the arcuate needle is passable between the first arcuate needle passer and the second arcuate needle passer and includes a first latching feature adapted to releasably secure the arcuate needle to the first arcuate needle passer and a second latching feature adapted to releasably secure the arcuate needle to the second arcuate needle passer.

3. The suture device of claim 2, wherein the first latching feature comprises a first pair of radially spaced protrusions disposed within a first portion of the arcuate needle and the second latching feature comprises a second pair of radially spaced protrusions disposed within a second portion of the arcuate needle.

4. The suture device of claim 2, wherein the arcuate needle further comprises a suture aperture disposed between the first latching feature and the second latching feature.

5. The suture device of claim 3, wherein the first needle passer comprises a first aperture complementary to a first protrusion of the first pair of protrusions and a second aperture complementary to a second protrusion of the first pair of protrusions.

6. The suture device of claim 5, wherein the first arcuate needle passer comprises a first pair of longitudinally aligned slots extending from the working end and towards the control end of the first arcuate needle passer, each of the first pair of longitudinally aligned slots extending through one of the first aperture and the second aperture such that the first arcuate needle passer is able to flex relative to the first aperture and the second aperture when not constrained by the first side of the arcuate suture ring.

7. The suture device of claim 3, wherein the second arcuate needle passer comprises a first aperture complementary to a first protrusion of the second pair of protrusions and a second aperture complementary to a second protrusion of the second pair of protrusions.

8. The suture device of claim 7, wherein the second arcuate needle passer comprises a second pair of longitudinally aligned slots extending from the working end and towards the control end of the second arcuate needle passer, each of the second pair of longitudinally aligned slots extending through one of the first aperture and the second aperture such that the second arcuate needle passer is able to flex relative to the first aperture and the second aperture when not constrained by the second side of the arcuate suture ring.

9. The suture device of claim 1, wherein the suture ring extends in a circle from a first open end to a second open end, the first open end and the second open end spaced apart a distance that permits tissue to extend therebetween.

10. The suture device of claim 9, wherein the annular channel has a circular cross-sectional profile except for a first region proximate the first open end and a second region proximate the second open end.

11. The suture device of claim 10, wherein the first region and the second region each have an ovoid cross-sectional profile that allows the first arcuate needle passer and/or the second needle passer to begin to flex as the first arcuate needle passer exits the first open end and/or the second arcuate needle passer exits the second open end.

12. The suture device of claim 1, wherein the first control element enters the first side of the arcuate channel substantially parallel to a tangent of the first arcuate needle passer proximate where the first control element is secured to the first arcuate needle passer.

13. The suture device of claim 1, wherein the second control element enters the second side of the arcuate channel substantially parallel to a tangent of the second arcuate needle passer proximate where the second control element is secured to the second arcuate needle passer.

14. The suture device of claim 2, further comprising a first tubular member housing the first control element and a second tubular member housing the second control element.

15. A suture device adapted to be used in combination with an endoscope, the suture device comprising:
    a suture ring having a first side and a second side, and defining an arcuate channel extending within the suture ring;
    a first tubular member comprising a curved distal portion that curves in a direction opposed to a direction of curvature of the first side of the suture ring;
    a second tubular member comprising a curved distal portion that curves in a direction opposed to a direction of curvature of the second side of the suture ring;
    a first arcuate needle passer slidingly disposed within a first side of the arcuate channel,
    a second arcuate needle passer slidingly disposed within a second side of the arcuate channel;
    a first control element disposed within the first tubular member and operably coupled to the first arcuate needle passer;
    a second control element disposed within the second tubular member and operably coupled to the second arcuate needle passer; and
    an arcuate needle passable between the first arcuate needle passer and the second arcuate needle passer by manipulating the first control element and the second control element;
    wherein the first control element and the second control element cross over each other upon entering the arcuate channel of the suture ring.

16. The suture device of claim 15, wherein the first needle passer comprises a working end adapted to releasably secure the arcuate needle.

17. The suture device of claim 16, wherein the first arcuate needle passer comprises a first pair of longitudinally aligned slots extending through the working end of the first needle passer such that the working end of the first needle passer is able to flex when not constrained by the first side of the arcuate suture ring.

18. The suture device of claim 15, wherein the second arcuate needle passer comprises a working end adapted to releasably secure the arcuate needle.

19. The suture device of claim 18, wherein the second arcuate needle passer comprises a second pair of longitudinally aligned slots extending through the working end of the second arcuate needle passer such that the working end of the second arcuate needle passer is able to flex when not constrained by the second side of the arcuate suture ring.

20. A suture device adapted to be used in combination with an endoscope, the suture device comprising:
    an end cap ring adapted to be secured to a distal end of an endoscope;
    a C-shaped suture ring secured to the end cap ring, the C-shaped suture ring having a first side and a second side, and defining an arcuate channel extending within the suture ring;
    a first arcuate needle passer slidingly disposed within a first side of the arcuate channel,
    a second arcuate needle passer slidingly disposed within a second side of the arcuate channel;
    a first control element that is adapted to enter the first side of the arcuate channel substantially parallel to a tangent of the first needle passer proximate where the first control element is secured to the first needle passer;
    a second control element that is adapted to enter the second side of the arcuate channel substantially parallel to a tangent of the second needle passer proximate where the second control element is secured to the second needle passer; and
    an arcuate needle passable between the first arcuate needle passer and the second arcuate needle passer by manipulating the first control element and the second control element;
    wherein the first control element and the second control element cross over each other upon entering the arcuate channel of the C-shaped suture ring.

\* \* \* \* \*